United States Patent [19]

Griffiths et al.

[11] Patent Number: 5,180,826

[45] Date of Patent: Jan. 19, 1993

[54] PROCESS FOR THE PRODUCTION OF 1-(N-METHANESULFONYL-N-METHYLAMINOSULFONYL)-3-(2-PYRIMIDYL) UREA DERIVATIVES

[75] Inventors: Gareth Griffiths, Visp; Aleksander Warm, Visperterminen; Felix Previdoli, Brig; Gary Ryan, Visp, all of Switzerland

[73] Assignee: Lonza Ltd., Gampel/Valais, Switzerland

[21] Appl. No.: 854,536

[22] Filed: Mar. 19, 1992

[30] Foreign Application Priority Data

Mar. 21, 1991 [CH] Switzerland .......................... 871/91

[51] Int. Cl.$^5$ ............................................ C07D 239/42
[52] U.S. Cl. .................................. 544/332; 544/298; 544/320

[58] Field of Search ...................... 544/332, 320, 298

[56] References Cited

FOREIGN PATENT DOCUMENTS 0131258 1/1985 European Pat. Off. .

*Primary Examiner*—John M. Ford
*Attorney, Agent, or Firm*—Fisher, Christen & Sabol

[57] ABSTRACT

A process for the production of 1-(N-methanesulfonyl-N-methylaminosulfonyl)-3-(2-pyrimidyl) urea derivatives (MMSPH). In the process, methanesulfonylmethylamine (MMSA) is first converted with chlorosulfonylisocyanate (CSI) into a 1-methanesulfonyl-1-methyl-3-(N-methanesulfonyl-N-methylaminosulfonyl) urea derivative (MMMSH) and then the MMMSH is converted with a 2-aminopyridine into the end product.

8 Claims, No Drawings

PROCESS FOR THE PRODUCTION OF 1-(N-METHANESULFONYL-N-METHYLAMINOSULFONYL)-3-(2-PYRIMIDYL) UREA DERIVATIVES

BACKGROUND OF THE INVENTION 1. Field Of The Invention

The invention relates to a new process for the production of 1-(N-methanesulfonyl-N-methylaminosulfonyl)-3-(2-pyrimidyl) urea derivatives as well as a new intermediate product useful for their production. 2. Background Art The 1-(N-methanesulfonyl-N-methylaminosulfonyl)-3-(2-pyrimidyl) urea derivatives, hereinafter abbreviated as MMSPH, are used, for example, in the growth regulation of plants [European Published Patent Application No. 131,258]. A process for the production of MMSPH has already been described in European Published Patent Applicatior No. 131,258. In this process, starting from methanesulfonylmethylamine (MMSA) and chlorosulfonylisocyanate (CSI), methanesulfonyl-N-methylaminosulfonylisocyanate (MSMASI) is produced first. Then MSMASI is converted with 2-amino-4,6-dimethoxypyrimidine (ADMP) into the corresponding MMSPH. A serious drawback of this process lies in that fact that, because of the tendency toward autocatalytic decomposition of MSMASI, for safety reasons it can be used only to a limited extent, particularly since the reaction has to be performed at relatively high temperatures.

BROAD DESCRIPTION OF THE INVENTION

The main object of the invention is to eliminate the above-mentioned drawback of the prior art and to provide a better process with respect to safety.

Other objects and advantages of the invention are set out herein or are obvious herefrom to one skilled in the art.

The objects and advantages of the invention are achieved by the process and intermediate product of the invention.

The process for the production of MMSPH, according to the invention, in which $R_1$, $R_2$ and $R_3$ are the same or different and each is a hydrogen atom, a $C_1$–$C_4$ alkoxy group, a hydroxyl group or a halogen atom, is performed so that in the first stage MMSA of the formula:

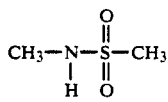

is converted with CSI into the 1-methanesulfonyl-1-methyl -3-(N-methanesulfonyl-N-methylaminosulfonyl) urea derivative (MMMSH) of the formula:

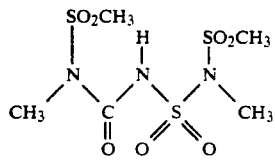

the latter is optionally isolated, and then, in a second stage, is converted with a 2-aminopyrimidine of the formula:

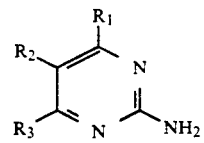

wherein $R_1$, $R_2$ and $R_3$ have the above-mentioned meaning, into the end product.

Preferably the conversion in the second stage is performed with 2-amino-4,6-dimethoxypyrimidine. Preferably the conversions in the first and second stages are performed at a temperature of 50° to 100° C. Preferably an inert solvent is used in the first and second stages. Preferably the conversion in the second stage is performed without isolation of the intermediate product of formula III of the conversion in the first stage.

The invention also includes 1-methanesulfonyl-1-methyl -3-(N-methanesulfonyl-N-methylaminosulfonyl) urea according to the formula:

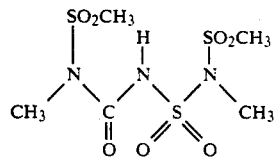

DETAILED DESCRIPTION OF THE INVENTION

Suitably the reaction in the first stage is performed with 2 mol of MMSA, relative to 1 mol of CSI. Suitably the reaction in the first stage is performed at a temperature of 50° to 100° C., preferably at a temperature of 50° to 85° C. The first stage is suitably performed in an inert solvent. Aromatic hydrocarbons, aliphatic or aromatic halogenated hydrocarbons, ethers and low-boiling alkanes can be used as the inert solvent. As representatives of these inert solvents chlorobenzene, hexane, toluene or dichloroethane, for example, can be used. Preferably dichloroethane is used as the inert solvent.

The thus obtained MMMSH of formula:

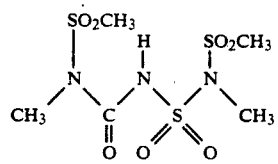

is a component of the invention.

The MMMSH is converted by reaction with 2-aminopyrimidine into MMSPH. ADMP is suitably used as 2-aminopyrimidine. Suitably the ADMP is used equimolar with the MMMSH in the second stage. The reaction in the second stage is suitably performed at a temperature of 50° to 100° C., preferably of 50° to 85° C. Suitably the second, as the first stage, is performed in an inert solvent. The inert solvents can be the same as described above for the first stage. After a usual reaction time of 3 to 24 hours, the MMSPH can be obtained by precipitation.

The process for the production of MMSPH can be performed with or without isolation of the MMMSH.

In a preferred embodiment, the process is performed as a one-pot variant without isolation of the intermediate product and the accumulating MMSA is recycled into the second stage.

EXAMPLE 1

Production Of MMMSH

A solution of MMSA (20 g, 183.3 mmol) in chlorobenzene (60 ml) was heated to 80° C. At this temperature CSI (13 g, 8 ml, 91.1 mmol) was instilled within 15 minutes. After stirring for 2 more hours at 80° C., a precipitate was obtained that was then subjected to suction. These crystals were then washed with n-hexane and dried at 20° C. in a vacuum (50 mbar). 26.9 g of product was obtained as white crystals, corresponding to a yield of 90.5 percent, relative to the CSI used. Other data concerning the intermediate MMMSH are:

| Melting point: 126° to 128° C. CHN-analysis: | | | | | |
|---|---|---|---|---|---|
| Cld.: | C 18.57% | H 4.00% | N 12.989% | | |
| Found: | C 18.4% | H 3.8% | N 13.1% | | |
| $^1$H-NMR (CDCl$_3$, 300 MHz) $\delta$ in ppm: | | | 10.12 | (br. s, 1H) | |
| | | | 3.52 | (s, 3H) | |
| | | | 3.31 | (s, 6H) | |
| | | | 3.24 | (s, 3H) | |

EXAMPLE 2

Production Of MMSPH

MMMSH (4.52 g, 12.7 mmol) was added as solid to a solution of ADMP (2.73 g, 12.7 mmol) in chlorobenzene (20 ml), at 50° C. The reaction mixture was stirred for 5 more hours at 55° C. and cooled to room temperature, and the product precipitated. This precipitate was subjected to suction and dried in a vacuum (50 mbar) at 50° C. 4.47 g of MMSPH was obtained, with a purity of 90.7 percent according to HPLC, corresponding to a yield of 86.4 percent, relative to the ADMP used.

EXAMPLE 3

Production Of MMSPH As One-Pot Variant

A solution of MMSA (99.48 percent) (21.94 g, 0.2 mol) in dichloroethane (100 ml) was heated to 80° C. At this temperature, CSI (11.32 g, 0.08 mol) was instilled within 15 minutes. The reaction mixture was then stirred for 2 hours at 80° C. The reaction mixture was then cooled to 50° C. Then a solution of ADMP (99.2 percent) (15.02 g, 0.1 mol) in dichloroethane (20 ml) was added to this yellow solution and a precipitate formed. The reaction mixture was then stirred for 2 hours at 50° C. The suspension was cooled and the precipitate filtered off. The solid was washed with methanol (3×30 ml). The product was dried at 35° C. in a vacuum (25 mbar). 26.95 g of product in the form of white crystals was obtained with a purity of 100 percent (according to HPLC), corresponding to a yield of 91 percent, relative to the CSI used. Other data concerning the MMSPH was:

| Melting point: 160.5° to 162.5° C. CHN-analysis: | | | |
|---|---|---|---|
| Cld.: | C 29.3%, | H 4.1%, | N 19.0% |
| Found: | C 29.1%, | H 4.1%, | N 18.8% |

| Melting point: 160.5° to 162.5° C. CHN-analysis: |
|---|
| IR (0.5 percent in KBr): 1711, 1616, 1572, 1512 cm$^{-1}$ |
| $^1$H-NMR (DMSO, 300 MHz) $\delta$ in ppm :  13.1 (br. s, 1H) |
|   10.9 (s, 1H) |
|   6.02 (s, 1H) |
|   3.9 (s, 6H) |
|   3.43 (s, 3H) |
|   3.38 (s, 3H) |

What is claimed is:

1. A process for the production of 1-(N-methanesulfonyl-N-methylaminosulfonyl)-3-(2-pyrimidyl) urea derivatives of the formula:

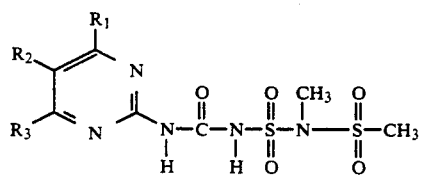

wherein $R_1$, $R_2$ and $R_3$ are the same or different and each is a hydrogen atom, a $C_1$-$C_4$ alkoxy group, a hydroxyl group or a halogen atom, comprising: in a first stage, converting methanesulfonylethyl amine of the formula:

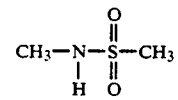

with chlorosulfonylisocyanate into a 1-methanesulfonyl-1-methyl -3-(N-methanesulfonyl-N-methylaminosulfonyl) urea derivative of the formula:

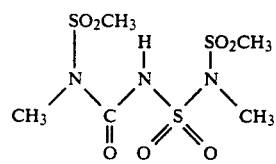

and then, in a second stage, converting the 1-methanesulfonyl-1-methyl-3-(N-methanesulfonyl-N-methylaminosulfonyl) urea derivative with a 2-aminopyrimidine of formula:

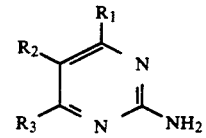

wherein $R_1$, $R_2$ and $R_3$ have the above-mentioned meaning, into the end product.

2. The process according to claim 1 wherein the reaction in the second stage is performed with 2-amino-4,6-dimethoxypyrimidine.

3. The process according to claim 2 wherein the conversions in the first and second stages are performed at a temperature of 50° to 100° C.

4. The process according to claim 3 wherein an inert solvent is used in the first and second stages.

5. The process according to claim 4 wherein the conversion in the second stage is performed without isolation of the intermediate product of formula III from the conversion in the first stage.

6. The process according to claim 1 wherein the conversions in the first and second stages are performed at a temperature of 50° to 100° C.

7. The process according to claim 1 wherein an inert solvent is used in the first and second stages.

8. The process according to claim 1 wherein the conversion in the second stage is performed without isolation of the intermediate product of formula III from the conversion in the first stage.

* * * * *